United States Patent [19]

Puchalski et al.

[11] Patent Number: 5,043,155

[45] Date of Patent: Aug. 27, 1991

[54] EMULSIFYING COMPOSITIONS INCLUDING AMPHIPATHIC EMULSIFYING AGENTS

[75] Inventors: Eugene Puchalski, Jersey City; George Deckner, Westfield; Emil F. Schneider, Long Branch, all of N.J.

[73] Assignee: Richardson-Vicks Inc., Shelton, Conn.

[21] Appl. No.: 532,357

[22] Filed: May 31, 1990

Related U.S. Application Data

[63] Continuation of Ser. No. 154,644, Feb. 10, 1988, abandoned.

[51] Int. Cl.$^5$ .................... A61K 31/74; B01J 13/00; C11D 17/00
[52] U.S. Cl. ..................... 424/78; 252/312; 252/548; 252/174.15; 252/174.23; 252/DIG. 5; 514/938
[58] Field of Search ............. 252/312, 174.15, 174.23, 252/DIG. 5, 548; 514/938; 424/78

[56] References Cited

U.S. PATENT DOCUMENTS

| | | | |
|---|---|---|---|
| 3,925,242 | 12/1975 | Sagi et al. | 252/312 |
| 3,998,753 | 12/1976 | Antoshkiw et al. | 252/312 |
| 4,380,503 | 4/1983 | Koerner et al. | 252/312 |
| 4,481,185 | 11/1984 | Grollier et al. | 252/312 |
| 4,735,742 | 4/1988 | Ansmann | 252/312 |
| 4,741,855 | 5/1988 | Grote et al. | 252/312 |
| 4,798,682 | 1/1989 | Ansmann | 252/312 |

OTHER PUBLICATIONS

Clayton, "Theory of Emulsions", p. 376, 1943.

*Primary Examiner*—Catherine S. Kilby Scalzo
*Attorney, Agent, or Firm*—Lerner, David, Littenberg, Krumholz & Mentlik

[57] ABSTRACT

The present invention relates to emulsion compositions and methods for preparing these emulsion compositions which employ amphipathic emulsifying agents and high shear polymeric emulsion techniques and which may be used for the preparation of a great variety of emulsion compositions. In particular, the method provides for the preparation of hybrid products which effectively cleanse and also leave a highly protective substantive residue on the skin.

8 Claims, No Drawings

EMULSIFYING COMPOSITIONS INCLUDING AMPHIPATHIC EMULSIFYING AGENTS

This is a continuation of application Ser. No. 154,644 filed Feb. 10, 1988, now abandoned.

FIELD OF THE INVENTION

This invention relates in general to the preparation of a variety of emulsion compositions, and more particularly, to emulsion compositions and methods for preparing these emulsion compositions which employ amphipathic emulsifying agents and high shear polymeric emulsion techniques. The emulsion compositions of this invention although applicable to a variety of applications, and particularly applicable to and are therefore described in connection with the preparation of such emulsion compositions useful for the prevention of diaper dermatitis and the like.

BACKGROUND OF THE INVENTION

Diaper dermatitis is believed to be caused by the prolonged contact of the skin with body waste. The exact component or components of urine and feces responsible for diaper dermatitis has not been identified. Factors which have been suspected of causing diaper dermatitis include ammonia, moisture, bacteria, urine pH, and *Candida albicans*. Because these various suspected factors have different properties and require different therapies, the most effective method of treating diaper dermatitis has been the application of a topical protective barrier agent between the skin and the body waste.

Common protective topically applied barrier agents and the ingredients they contain include the following: Caldesene ® Powder (calcium undecylenate, 10%, fragrance, and talc) and Ointment (petrolatum, 53.9%, and zinc oxide, 15%); Desitin ® Ointment (zinc oxide, 40%, and cod liver oil, vitamins A and D, in a petrolatum-lanolin base, Leeming Division of Pfizer, Inc.); Balmex ® Baby Powder (Balsan ®, a specially purified balsam, Peru, zinc oxide, talc, starch, and calcium carbonate), Ointment (Balsan ®, vitamins A and D, zinc oxide and bismuth subnitrate in an ointment base containing silicone) and Lotion (Balsan ®, lanolin oil, a nonsensitizing, dewaxed moisturizing fraction and silicone).

Other lotions, creams and ointments used in the treatment of diaper dermatitis and the active ingredients they contain include the following; Baby Magic Baby Lotion (Mennan) benzalkonium chloride; Johnson's Baby Cream (Johnson & Johnson) 2% dimethicone and Lotion; Diaparene Peri-Anal Medicated Ointment (Glenbrook Labs) 0.1% methylbenzethonium chloride; Suave Baby Care Skin Lotion (Helene Curtis); and Methakote DiaperRash Cream (Syntex) protein hydrolysate composed of L-leucine, isoleucine, L-methionine, L-phenylalanine, L-tyrosine, DL-methionine, cysteine hydrochloride, benzethonium chloride and talc, U.S. Pat. No. 3,061,512.

In addition to protective barrier agents, baby wipes are also used in the treatment of diaper dermatitis. Baby wipes are premoistened, disposable towelettes used primarily during diaper changes for cleansing. The wipe is usually constructed of non-woven wood pulp (approximately 85%) and another fiber such as polyester bonded with a styrene butadiene rubber latex. Wipes are generally moistened with water (over 95%) and contain various combinations of humectants, emollients, surfactants, preservatives and scents.

Baby wipes currently available and ingredients they contain include the following: Baby Fresh (Scott); Johnson's Baby Wash Cloths (Johnson & Johnson); Wet Ones (Lehn and Fink Products Group, Division of Sterling Drug, Inc.) natural aloe, U.S. Pat. Nos. 4,017,002 and 4,337,876; Diaperene Baby Wash Cloths with Lanolin (Glenbrook Labs, Division of Sterling Drug) U.S. Pat. No. 4,017,002; Tender Wipes (Young's Drug Products) benzethonium chloride; and Chubs Thick Baby Wipes (Lehn and Fink Products Group, Division of Sterling Drug, Inc.) aloe, U.S. Pat. Nos. 4,017,002 and 4,337,876;

Various combinations of the following ingredients are used in baby wipe products: water, SD alcohol 40, benzyl alcohol, propylene glycol, aloe vera gel, PEG-60 lanolin, PEG-75 lanolin, PEG-85 lanolin, sodium nonoxynol-9 phosphate, sorbic acid, oleth-10, oleth-20, fragrance, citric acid, disodium phosphate, DH DM hydantoin, sodium phosphate, benzalkonium chloride, methylparaben, propylparaben, butylparaben, sodium hydroxide, octoxynol-9, simethicone, polysorbate-20, cocoamphocarboxyglycinate, methylchloroisothiazolinone, methylisothiazolinone, trisodium EDTA, Quaternium-15, lauramine oxide, mineral oil, glycerine, PEG-8 stearate, petrolatum, Quaternium-27 and 2-bromo-2-nitropropane-1,3-diol.

Treatment of diaper dermatitis usually requires the combination of wipes and a protective barrier agent. The wipes are used initially, for cleansing, and then a barrier agent is applied for skin protection. Baby wipes currently available do not leave after application substantive or wash-resistant residues to protect the skin. Barrier agents are generally greasy and unappealing and are not effective cleansing agents. In addition, the use of some barrier agents may actually promote excessive skin hydration which may result in increased skin friction thus aggravating diaper dermatitis.

TAKE OFF (Johnson & Johnson) is a wipe product which contains an emulsion composition formulated as a makeup remover but has no substantive or skin protective properties.

There is thus a need in the treatment of diaper dermatitis for a hybrid product which would effectively cleanse and also leave a substantive highly protective residue on the skin. It would also be desirable to be able to apply the hybrid product as a wipe. The product should cleanse and leave a protective residue which does not significantly reduce transepidermal moisture loss.

SUMMARY OF THE INVENTION

The present invention relates to emulsion compositions and methods for preparing these emulsion compositions which employ amphipathic emulsifying agents and high shear polymeric emulsion techniques. The invention provides a method for the preparation of a great variety of emulsion compositions, in particular, for the preparation of compositions that cleanse and also leave a highly protective substantive residue on the skin. Such compositions are useful in a great variety of therapies, for example, in the treatment of diaper dermatitis.

One aspect of the present invention provides an oil in water emulsion composition comprising an oil, present in the range of from about 3.0% to about 40% by weight of the composition, and an amphipathic emulsifying agent present in the range of from about 0.02% to about 2.0% by weight of the composition, in water, which has been subjected to high shear polymeric emulsion forces.

Another aspect of the present invention provides a method for the preparation of an oil in water emulsion composition which comprises the steps of emulsifying an oil, present in the range of from about 3 to about 40% by weight of the composition, and an amphipathic emulsifying agent present in the range of from about 0.02 to about 2.0% by weight of the composition, in water, by high shear polymeric emulsion forces.

DESCRIPTION OF THE INVENTION

The present invention relates to emulsion compositions and methods for preparing these emulsion compositions which employ amphipathic emulsifying agents and high shear polymeric emulsion techniques (HSPE). The oil-in-water emulsion compositions of the present invention are highly substantive, safe, stable, and economical products.

The emulsifying agents which may be used in the present invention exhibit amphipathic properties and are capable of primary emulsification of oil-in-water emulsions. The emulsifiers should be capable of rapidly inverting or de-emulsifying the emulsion to form an oil film upon application to the skin.

The emulsifying agents which are useful in the present invention include Carbopol (Carbomer) 940, Carbopol 934, Carbopol 941, Carbopol 1342 and Gulf Polymer P18 (octadecene/maleic anhydride copolymer) and combinations thereof.

Other useful emulsifying agents include $C_{12}-C_{22}$ alkyl-substituted acrylic acid copolymers, either alone or in combination with the above emulsifying agents, where the alkyl group is lauric, myristic, palmitic, stearic, oleic, linolenic or isostearic. Still other useful emulsifying agents, either alone or in combination with the above emulsifying agents, include stearyl ether/maleic anhydride copolymers (Gantroz AN-8194) and allyl stearate/valeric anhydride copolymer (Mexomere PG).

The emulsifying agents which are useful in the present invention may be present in the range of from about 0.02% to about 2.0%, and preferably from about 0.8% to about 1.4%, by weight of the emulsion composition.

The oils (emollients or barrier aids) which are useful in the present invention include dimethicone (Dow Corning 200 Fluids), dimethicone and trimethylsiloxysilicate (Dow Corning 593 Fluid), phenyl dimethicone (Dow Corning 556 Fluid), stearoxy dimethicone (SWS 755 Wax), cyclomethicone (Dow Corning 344 or 345 Fluid, Union Carbide 7158 Fluid, GE SF1173, 1202 or 1204, Ganex U216 or U220), cyclomethicone and dimethicone (Dow Corning X2-1401) and dimethicone (GE SE30, 76 gums, ultra high molecular weight dimethicone, greater than 1,000,000 centistokes (cs)) or combinations thereof.

The oils which are useful in the present invention may be present in the range of from about 3.0 to about 40%, and preferably from about 27% to about 33%, by weight of the emulsion composition.

The emulsion compositions of the present invention are subjected to high shear polymeric emulsion forces. A turbine mixer and in-line homogenizer utilizing tandem rotor-stators (two turbines and mating stators in tandem on a single shaft) may be used for in-line continuous high-speed high-shear homogenizing-mixing, emulsifying and rapid dispersing. Shaft-rotor speeds in the range of about 5,000 to about 15,000 may be used. A shaft-rotor speed of about 10,000 rpm is preferred.

Optional ingredients which may be used in the present invention include preservatives, antifungal agents, skin protectants, moistening/humectant agents, pH adjusters, powders and the like.

The preservatives which may be used in the present invention include Quaternium 15 (Dowicil 200), methyl paraben (Tegosept M), propyl paraben (Tegosept P), DHDM hydantoin (Glydant), benzyl alcohol, methylchloroisothiazolinone and methylisothiazolinone (Kathon CG), butyl paraben (Tegosept B), imidazolidinyl urea (Germall 115), diazolidinyl (Germall II), and sequestrene No. 2, No. 3 or No. 4 (Disodium EDTA, trisodium EDTA, tetrasodium EDTA, respectively).

The antifungal agents which may be used in the present invention include chlorobenzyl alcohol (Myacide SP), mycostatin (Nystatin), miconazole (Ohasept Extra), parachloro meta zylenol, undecyclenic acid, calcium undecyclenate and zinc undecyclenate.

The skin protectants which may be used in the present invention include allantoin, zinc carbonate, zinc oxide, zinc acetate, cocoa butter, shark liver oil, kaolin, calamine, aluminum hydroxide gel and glycerin.

The moistening/humectant agents which may be used in the present invention include glycerin, propylene glycol, PEG 8 (Carbowax 400), sorbitol (Sorbo 70%), polyglyceryl methacrylate and propylene glycol (Lubrajel), proline and sodium PCA (Agidew NSO).

The agents which may be used to adjust pH in the present invention include triethanolamine (TEA, Quadrox), sodium hydroxide, potassium hydroxide, citric acid, lactic acid, glucamine (Desamine) and arginine.

The powders which may be used in the present invention include cornstarch, rice starch, talc, mica, starch modified polyacrylic acid, nylon powder, silicone treated nylon and silicon treated talc.

A preferred emulsion composition comprises Silicone 200 (350 cs and 1,000 cs) (5%), Carbopol 1342 (0.15%), Kathon CG (0.10%), 99% Triethanolamine (0.20%), and Sequestrene No. 2 (0.10%) in water (about 95%).

The emulsion compositions of the present invention may be applied with a wipe by impregnating or otherwise contacting the emulsion composition with a web which may be a cellulosic wipe.

Oil in water emulsion compositions prepared with amphipathic emulsifiers and subjected to high shear polymeric emulsification have advantages over emulsion compositions prepared using conventional techniques which include the following:

1. Emulsion compositions of the present invention de-emulsify when applied to the skin helping to increase the substantivity, or wash resistance, of the composition on the skin. This resulting protective substantive barrier significantly reduces wet and dry skin friction and protects the skin against the irritating effects of chemicals. De-emulsification of the compositions also results in a pleasant feel on the skin.

2. Emulsion compositions of the present invention may be prepared in a highly concentrated form resulting in significant cost advantage. The emulsion compositions may be prepared as a 10-fold concentrate and then diluted with water using low shear processing equipment to complete preparation of the composition. Both the emulsion concentrate and the diluted formula were found to be stable at 48° C., 25° C., 4° C. and −15° C. for over one month. Such emulsion stability is extremely difficult to achieve with compositions prepared by conventional emulsion technology, especially for lotions with viscosity less than 100 cps.

3. Emulsion compositions of the present invention require only very low concentrations of emulsifying agents (Carbopol 1342, 0.15%) to achieve emulsion stability. In addition to being economical, low emulsifying agent levels help reduce the irritation potential of the compositions. The primary skin irritation on 105 subjects was shown to be extremely low using the Repeat Insult Patch Test (RIPT). A chamber scarification test was also performed and the results showed that the emulsion compositions of the present invention were as gentle as physiological saline on human abraded skin.

4. Emulsion compositions of the present invention have significantly more uniform moisture profiles or gradients when absorbed onto a web than emulsion compositions prepared by conventional techniques.

5. Emulsion compositions of the present invention significantly improve the cosmetic properties of the web. The tactile properties on skin of the instant compositions impregnated on a wipe were judged to be greatly improved over that of other emulsion compositions impregnated on a wipe (soft, smooth, tacky, moisturized). Emulsion compositions of the present invention also showed a 34% reduction in the coefficient of friction on webs versus conventional emulsion compositions. This data correlated well with sensory panel testing data.

6. Emulsion compositions of the present invention do not significantly affect the physical strength of the web. Emulsions prepared by a conventional means may chemically interact with the web binder and cause a significant reduction in the physical strength of the web.

The methods employed to prepare the emulsion compositions of the present invention are applicable to the preparation of a great variety of emulsion compositions. Such compositions include low irritation, wash resistant lotions, creams, sprays and clear gels; high performance, unique feeling, skin treatment and sunscreen products; alcohol-free, solubilizer-free perfumes, colognes, after-shave products; ultra gentle baby products; hair conditioners; substantive toners; highly effective, gentle makeup removers; and many non-cosmetic products.

The following examples are illustrative:

EXAMPLE 1

A particularly preferred emulsion composition in the form of a barrier lotion useful for the treatment of diaper dermatitis was prepared in accordance with the present invention having the following composition:

| Trade Name | CTFA Name | Parts by Weight |
| --- | --- | --- |
| 10-Fold Concentrate Formula | | |
| Deionized Water | Water | 63.275 |
| 200 Fluid (350 cs) | Dimethicone | 24.000 |
| 200 Fluid (1000 cs) | Dimethicone | 10.000 |
| Carbopol 1342 | Carbomer 1342 | 1.500 |
| Triethanolamine | TEA | .125 |
| Kathon CG | Methychloroiso-thiazolinone (and Methyisothiazo-linone | .100 |
| Dilution Formula | | |
| Deionized Water | Water | 89.60 |
| Concentrate | (See Above) | 10.00 |
| Disodium ethylene diamine tetraacetic acid | Disodium EDTA | .10 |
| Triethanolamine | TEA | .10 |

-continued

| Trade Name | CTFA Name | Parts by Weight |
| --- | --- | --- |
| Kathon CG | Methychloroiso-thiazolinone (and Methyisothiazo-linone | .— |

EXAMPLE 2

A preferred emulsion composition in the form of a barrier lotion useful for the treatment of diaper dermatitis was prepared in accord with the present invention having the following composition:

| Trade Name | CTFA Name | Percent | Range |
| --- | --- | --- | --- |
| Deionized Water | Water | 94.03 | 70–99 |
| Sequestrene No. 2 | Disodium EDTA | .10 | .01–.50 |
| Carbopol 1342 | Carbopol 1342 | .15 | .02–1.5 |
| Silicone 200 (350 cs) | Dimethicone | 2.40 | 1–10 |
| Silicone 200 (1000 cs) | Dimethicone | 1.00 | .5–10 |
| Deionized Water | Water | 1.00 | |
| Kathon CG | Methychloroiso-thiazolinone (and Methyisothiazo-linone | .11 | .02–.12 |
| Deionized Water | Water | 1.00 | |
| 99% Triethanolamine | TEA | .21 | .05–3.0 |

EXAMPLE 3

A preferred emulsion composition in the form of a barrier lotion concentrate useful for the treatment of diaper dermatitis was prepared in accord with the present invention having the following composition;

| Number | Trade Name | Percent |
| --- | --- | --- |
| A-1 | Deionized Water | 65.768 |
| A-2 | Sequestrene NA$_2$ | 0.240 |
| B-3 | Deionized Water | 1.000 |
| B-4 | Triethanolamine 99% | 0.092 |
| C-5 | Kathon CG | 0.100 |
| D-6 | Volatile Silicone | 12.000 |
| D-7 | Carbopol 1342 | 1.100 |
| D-8 | Silicone 200 (350 cs) | 12.000 |
| D-9 | Silicone 200 (1000 cs) | 7.700 |

MIXTURE D

Volatile Silicone (D-6) was charged to a feed kettle equipped with a propeller mixer. Vigorous mixing was commenced. Carbopol 1342 (D-7) was added and when completely wet-out, silicone 200 (350cs) (D-8) was added and propeller mixed 5 minutes. Silicone 200 (1000 cs) (D-9) was then added to the mixture and propeller mixed.

MIXTURE A

Deionized water was charged to the main kettle equipped with a turbine mixer and in-line homogenizer utilizing tandem rotor-stators. Turbine mixing was commenced 10,000 rpm), Sequestrene NA$_2$ was added (A-2), and turbine mixing was continued 5 minutes.

MIXTURE B

Deionized water (B-3) and triethanolamine (B-4) were premixed with the propellar mixer. When mixture A and mixture B were uniform, mixture B was added to mixture A and turbine mixed 10–15 minutes. When the mixture of A, B and mixture D were uniform, Kathon CG (C-5) was added to the mixture of A and B. The mixture of A and B and C. was turbine mixed 1 minute. The recirculation of mixture A and B and C. thru the in-line homogenizer was commenced. Mixture D was introduced through an "I" connection on the recirculation loop. When the addition was complete, the feed kettle was rinsed with the withheld silicone. Turbine mixing and recirculation was continued thru the in-line homogenizer for 60 minutes or until the Carbopol was dispersed. The temperature was kept below 30° C. When the mixture was uniform, the recirculation thru the in-line homogenizer was stopped. Turbine mixing was continued 60 minutes. The mixture was pumped and strained.

As these and other variations, combinations and modifications of the features described above can be utilized without departing from the spirit of this invention, the foregoing description of the preferred embodiments should be taken by way of illustration rather than by way of limitation of the invention as defined in the claims.

I claim:

1. A stable concentrated oil in water emulsion composition dilutable with water to form a stable diluted oil in water emulsion admixture for cleaning and leaving a protective substantive residue on the skin of a person upon deemulsification thereof, said composition comprising only a silicon based oil present in the range of from about 3.0% to 40% by weight of said composition and an amphipathic emulsifying agent present in the range of from about 0.02% to 2.0% by weight of said composition, said oil and said amphipathic emulsifying agent admixed with water under high shearing polymeric emulsion forces to form a stable concentrated oil in water emulsion composition which resists deemulsification during storage, said composition dilutable with water using low shearing polymeric emulsion forces to form a stable diluted oil in water emulsion admixture which resists deemulsification during storage having water present in an amount greater than about 70% by weight of said composition and a viscosity of less than about 100 cps.

2. The composition according to claim 1 wherein the emulsifying agent is selected from the group consisting of Carbopol 940, Carbopol 934, Carbopol 941, Carbopol 1342, octadecene-maleic anhydride copolymers, stearyl ether-maleic anhydride copolymers, alkyl stearate-valeric anhydride copolymers and $C_{12}$–$C_{22}$ alkyl-substituted acrylic acid copolymers where the alkyl group is lauric, myristic, palmitic, stearic, oleic, linolenic or isostearic, or combinations thereof.

3. The composition according to claim 2 wherein the emulsifying agent is present in the range of from about 0.8% to about 1.4% by weight of the composition.

4. The composition according to claim 1 wherein the oil is selected from the group consisting of dimethicone, dimethicone and trimethylsiloxy silicate, phenyl dimethicone, stearoxy dimethicone, cyclomethicone, cyclomethicone and dimethicone, or combinations thereof.

5. The composition according to claim 4 wherein the oil is present in the range of from about 27% to about 33% by weight of the composition.

6. The composition according to claim 1 wherein the high shear polymeric emulsion shaft-rotor speed is carried out at about 10,000 rpm.

7. The composition according to claim 1 wherein the emulsion comprises Silicone 200 (350 cts and 1,000 cts) (5%), Carbopol 1342 (0.15%), Kathon CG (0.10%), 99% Triethanolamine (0.20%), and Sequestrene No. 2 (0.10%) in water.

8. A stable diluted oil in water emulsion admixture formed from a stable concentrated oil in water emulsion composition for cleaning and leaving a protective substantive residue on the skin of a person upon deemulsification thereof, said composition comprising only a silicon based oil present in the range of from about 3.0% to 40% by weight of said composition and an amphipathic emulsifying agent present in the range of from about 0.02% to 2.0% by weight of said composition, said oil and said amphipathic emulsifying agent admixed with water under high shearing polymeric emulsion forces to form a stable concentrated oil in water emulsion composition which resists deemulsification during storage, said composition diluted with water using low sheering polymeric emulsion forces to form said stable diluted oil in water emulsion admixture which resists deemulsification during storage having water present in an amount greater than about 70% by weight of said composition and a viscosity of less than about 100 cps.

* * * * *